US008668337B2

(12) United States Patent
Waldorf et al.

(10) Patent No.: US 8,668,337 B2
(45) Date of Patent: Mar. 11, 2014

(54) SYSTEM FOR THE PHYSIOLOGICAL EVALUATION OF BRAIN FUNCTION

(75) Inventors: Ronald A. Waldorf, Beverly Hills, CA (US); Hirsch Handmaker, Scottsdale, AZ (US)

(73) Assignee: TBI Diagnostics LLC, Scottsdale, AZ (US)

( * ) Notice: Subject to any disclaimer, the term of this patent is extended or adjusted under 35 U.S.C. 154(b) by 70 days.

(21) Appl. No.: 13/450,230

(22) Filed: Apr. 18, 2012

(65) Prior Publication Data

US 2013/0278899 A1 Oct. 24, 2013

(51) Int. Cl.
*A61B 3/14* (2006.01)
*A61B 3/10* (2006.01)
*A61B 3/00* (2006.01)

(52) U.S. Cl.
USPC ............................ 351/209; 351/205; 351/246

(58) Field of Classification Search
USPC .................................................. 351/200–246
See application file for complete search history.

(56) References Cited

U.S. PATENT DOCUMENTS

| | | | |
|---|---|---|---|
| 5,649,061 A * | 7/1997 | Smyth ............................ 706/16 |
| 7,384,399 B2 | 6/2008 | Ghajar | |
| 7,614,745 B2 | 11/2009 | Waldorf et al. | |
| 7,651,224 B2 | 1/2010 | Wood et al. | |
| 7,665,845 B2 | 2/2010 | Kiderman et al. | |
| 7,708,700 B2 | 5/2010 | Ghajar | |
| 7,731,360 B2 | 6/2010 | MacDougall et al. | |
| 7,753,523 B2 | 7/2010 | Kiderman et al. | |
| 7,819,818 B2 * | 10/2010 | Ghajar ........................... 600/558 |
| 7,866,818 B2 | 1/2011 | Schroeder et al. | |
| 7,988,287 B1 * | 8/2011 | Butler et al. .................. 351/210 |
| 8,048,002 B2 | 11/2011 | Ghajar | |
| 2008/0049187 A1 | 2/2008 | Joos et al. | |
| 2010/0092049 A1 | 4/2010 | Schroeder et al. | |
| 2010/0094161 A1 | 4/2010 | Kiderman et al. | |

OTHER PUBLICATIONS

Donaghy et al.; "Eye movements in amyotrophic lateral sclerosis and its mimics: a review with illustrative cases," *J Neurol Neurosurg Psychiatry*, Dec. 2011; 82(1):110-116.
Ghajar, Jamshid; Eye-Tracking Rapid Attention Computation (Eye-TRAC), Dec. 2012.
Irving et al.; "Horizontal Saccade Dynamics across the Human Life Span," *Investigative Ophthalmology & Visual Science*, 2006; 47(6); 2478-2484.
Maruta et al.; "Visual tracking synchronization as a metric for concussion screening," *J Head Trauma Rehabil*, Dec. 2010; 25(4):293-305.

(Continued)

*Primary Examiner* — Mohammed Hasan
(74) *Attorney, Agent, or Firm* — Patton Boggs LLP

(57) ABSTRACT

The OculoKinetic Device is used to test an individual to evaluate brain functions and to identify the presence of a traumatic brain injury or disease which manifests itself through abnormal ocular responses to stimuli by using the high-speed tracking of an individual's eye movements, pupil size and reactivity, eye lid position and blink parameters and optionally along with other ocular elements, i.e., eyeball pressure, temperature, blood flow, etc. The eye movement stimulus protocol uses a target that moves in any direction of the two-dimensional plane and may use a color display or geometric shapes. In addition, the stimuli can be used in conjunction with cognitive testing, balance assessment, and other non-eye tests.

10 Claims, 8 Drawing Sheets

(56) References Cited

OTHER PUBLICATIONS

Ross et al.; "Saccadic eye movements in normal children from 8 to 15 years of age: A developmental study of visuospatial attention," *Journal of Autism and Developmental Disorders*, Jan. 1994; 24(4):413-431.

Zackon et al.; "Smooth pursuit in senescence: Effects of Target Acceleration and Velocity," *Acta Otolaryngol*, Jan. 1987; 104(3-4); 290-297.

\* cited by examiner

SYSTEM FOR THE PHYSIOLOGICAL EVALUATION OF BRAIN FUNCTION

FIELD OF THE INVENTION

This invention relates to a system that is used to test an individual to evaluate brain functions and to identify the presence of a traumatic brain injury or other diseases which manifest themselves through abnormal ocular responses to stimuli, where the system uses high-speed tracking of an individual's eye movements, pupil size and reactivity, eye lid position and blink parameters, and optionally along with other ocular elements, i.e., eyeball pressure, temperature, blood flow, etc.

BACKGROUND OF THE INVENTION

It is a problem in the field of brain injuries to provide a method and apparatus that can be used to quickly, accurately, and non-invasively evaluate an individual to identify the presence of Traumatic Brain Injury (TBI), and its variants, also known as Minimal Traumatic Brain Injury (mTBI), more commonly known as concussion (collectively termed "TBI" herein).

TBI is the leading cause of death and disability for America's youth. According to statistics from the Centers for Disease Control and Prevention (CDC), between one million and four million new brain injuries occur every year in America due to trauma in sports and recreational activities. More than 767,000 American youth visit the emergency room because of traumatic brain injuries each year. Of those, more than 80,000 are hospitalized and more than 11,000 die. This at-risk population is only now gaining recognition and awareness, as most youth sports activities take place with no health care professionals in attendance, and few programs are available to determine which players suffer a concussion or when they should return to play after this injury. While professional sports, such as the National Football League (NFL), Major League Baseball (MLB), and National Hockey League (NHL), are implementing safety and monitoring standards, even they are utilizing only one or two of the quartet of commercially available tests which are known to be of value for adequate assessment and management of patients with TBI: physical examination by a qualified healthcare professional; neurocognitive testing; balance assessment; and eye movement responses. The frequency and sequelae of concussions have garnered national and international media attention, and has reached epidemic proportions, with these events now documented to be of greatest significance in younger (6- to 14-year-old) athletes whose brains have not yet become fully developed ("myelinated"). Note that sequelae of TBI include headache and dizziness, anxiety, apathy, depression, aggression, cognitive impairments, personality changes, mania, and psychosis. Typically, a sequela is a chronic condition that is a complication of an acute condition that begins during the acute condition.

Prior scientific research shows that eye movements are affected by these types of traumatic events. Although the research presents findings which support this hypothesis, the presently available equipment, test protocols, and analysis protocols are limited in several important respects and fail to provide an effective tool for detecting and monitoring TBI, especially in a competitive sports field or combat setting.

BRIEF SUMMARY OF THE INVENTION

The present System For The Physiological Evaluation Of Brain Function (termed "OculoKinetic Device" or "Advanced VNG System" herein) provides a method and apparatus that is used to quickly, accurately, and non-invasively evaluate a test subject to identify the presence of Traumatic Brain Injury (TBI), and its variants, also known as Minimal Traumatic Brain Injury (mTBI), or a disease which manifests itself through abnormal ocular responses to stimuli. The OculoKinetic Device uses the high-speed tracking of a set of test subject's physiological parameters, which can include: eye movements, pupil size and reactivity, eye lid position and blink parameters, and optionally along with other ocular elements, i.e., eyeball pressure, temperature, blood flow, etc.

The following description uses TBI as the example to illustrate the operation of the present OculoKinetic Device, but it is not limited to these applications, since it should be noted that the following diseases have also been reported to manifest themselves via ocular abnormalities which are detectable on oculomotor examinations:

1. Alzheimer's Disease
2. Multiple Sclerosis
3. Parkinson's Disease
4. Amyotrophic Lateral Sclerosis (ALS)—"Lou Gehrig Disease"

Existing standard-of-care eye movement stimulus protocols include, but are not limited to:

1. Smooth Pursuit—tracking eye movement that follows either movement of a target in only a horizontal direction or movement of a target in only a vertical direction.
2. Gaze—gaze induced nystagmus occurs or is exacerbated as a result of changing one's gaze toward or away from a particular side which has an affected vestibular apparatus.
3. Saccade—tracking quick, simultaneous movements of both eyes in the same direction. The saccade target is usually presented either horizontally or vertically.
4. Optokinetic—The standard optokinetic stimulus is a series of stripes that can be moved either horizontally or vertically.

The nature of the equipment that produces these stimulus protocols, i.e., discrete light bars, dots on the wall, etc., test eye responses exclusively in the horizontal direction or exclusively in the vertical direction. This is limiting to a complete eye movement examination, since the eye has three pairs of eye muscles, each being controlled by a separate set of brainstem nuclei and neural pathways which allows the eye to move in any direction in a two-dimensional plane, including torsional eye movements, i.e., those about the visual axis.

In contrast, the OculoKinetic Device is able to not only do this "limited" testing but, in addition, has the capabilities to produce eye movement stimuli that move in any direction of the two-dimensional plane. For example, with a Smooth Pursuit test, instead of a target moving horizontally only or vertically only, it may move in a FIG. 8 pattern or a more complex, randomized pattern. The OculoKinetic Device test protocols also are not limited to just black and white images, but can include visual targets that my increase the accuracy of evaluating brain function by using colored dots, stripes, etc. In addition, the use of symbols is anticipated, where the ocular stimuli are geometric shapes, multi-colored images, flashing images, etc. Such diversity in target presentations are beneficial in the testing of younger athletes and children who are more inclined to look at and follow shapes and colors rather than just black and white dots or lines.

In addition, these types of "eye-catching" stimuli can be used in conjunction with cognitive testing. As one of many possibilities, the Saccade test could be done with dots of a certain color. The test subject is instructed to look only at blue dots. Some of the dots would be presented in blue, but others could be red, yellow, etc. By seeing how the test subject's eye moves or fails to move from colored dot to colored dot, and analyzing the "errors," a more accurate neuro-cognitive test of possible brain trauma may be established.

Finally, the eye movement protocol results, optionally coupled with results from other non-eye tests, i.e., balance, information from a physical exam, etc., can be used to compute a metric termed herein the "Waldorf Score," which scales the brain injury of the subject by incorporating a plurality of measured metrics. It is computed from the results of the various oculomotor tests at a minimum, ranging to a compilation of data such as, but not limited to, pupillography, balance test results, cognitive test results, plus metrics such as blood pressure, body temperature, etc., which can be taken from the eyeball. By knowing the "Waldorf Score" for a test subject at any point in time provides clinicians and other interested parties the ability to more easily understand the neurophysiological issues at hand.

To monitor the movements of the test subject's eyes, ocular measurement devices that are sensitive in the near infrared illumination spectrum are positioned in the field of vision of the test subject to record the test subject's eye movements during testing. These ocular measurement devices are housed in a test subject interface which can be in the form of any of several goggle or head-mounted configurations or positioned in a "Viewport." In addition, a stimulus presentation device is included in the test subject interface to display visual stimuli for the test subject. To maximize the efficacy of these measurements, it is imperative that the configuration of the ocular measurement devices, the stimulus presentation device, and the test subject be arranged in a manner that controls the ambient light impinging on the test subject's eyes, as well as the elimination of extraneous visual targets from the test subject's field of vision. All of this must be accomplished in an ergonomic manner such that the test subject can easily be tested in a quick and efficient manner, regardless of the environment around them, i.e., stadium field of play, combat zone, etc.).

The ideal system for the physiologic evaluation of brain function has the following features: self-diagnostics to ensure each test is being performed within pre-defined specification limits; ability to document the test subject, stimulus paradigms, and test results in a manner that meets the requirements for human subject medical applications; and it must meet the criterion for functional testing in ambient environments that are variable in terms of weather, temperature, noise, and other testing constraints.

BRIEF DESCRIPTION OF THE DRAWINGS

FIG. 2A represents a fixed installation typically found in an office; FIG. 2B represents a portable dome-shaped test subject interface, typically for field use; while FIG. 2C illustrates a cross-section view of typical components used to implement the test subject interface;

DETAILED DESCRIPTION OF THE INVENTION

Figure 1:
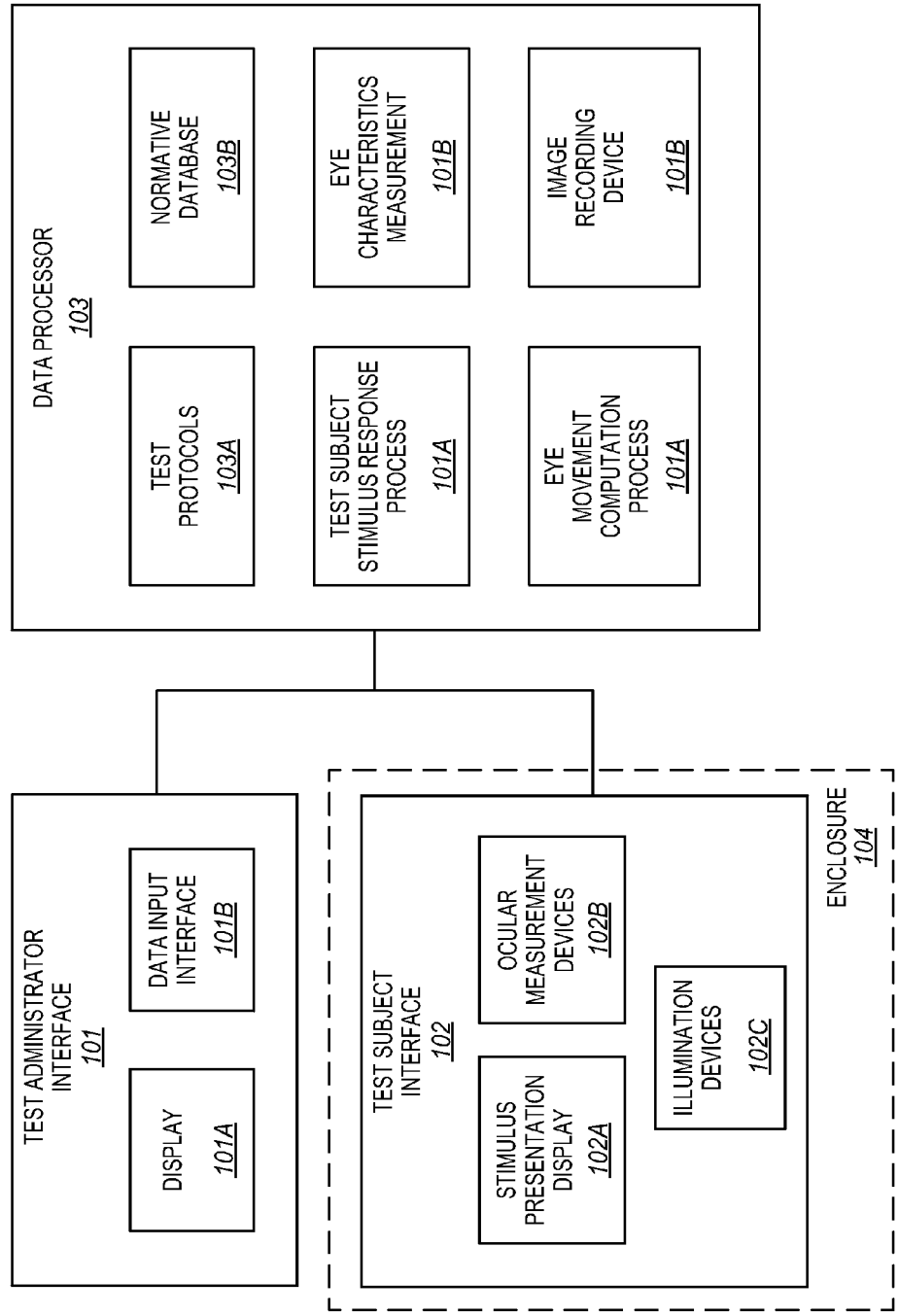
FIG. 1 illustrates, in block diagram form, the overall architecture of the present OculoKinetic Device.

The present OculoKinetic Device measures a set of test subject physiological parameters, which can include: an individual's eye movements, pupil size and reactivity, eye lid position and blink parameters, which optionally can be combined with other ocular elements, i.e., eyeball pressure, temperature, blood flow, etc. In order to determine the presence of abnormal ocular responses to visual stimuli, the OculoKinetic Device produces an eye movement stimulus protocol that moves a visual target in any direction of the two-dimensional plane on a stimulus presentation device. For example, with a Smooth Pursuit test, instead of a target moving in a horizontally only or a vertically only direction, it may move the visual target in a FIG. 8 pattern or a more complex, randomized pattern on the stimulus presentation device. The target representation is not limited to just black and white images. It may turn out that certain brain injuries and/or illnesses are more accurately detected by using colored dots, stripes, etc. In addition, the use of symbols in the visual target is anticipated, where the visual stimuli are geometric shapes, multi-colored images, flashing images, etc. Such diversity is beneficial in the testing of children who are more capable of describing shapes and colors than black and white dots or lines.

In addition, visual stimuli can be used in conjunction with cognitive testing. As one of many possibilities, the Saccade test could be done with dots of a certain color, i.e., blue. The test subject is instructed to look only at blue dots. Some of the dots would be presented in blue, but others could be red, yellow, etc. By seeing how the test subject's eye moves or fails to move, and analyzing the "errors," a more accurate test of possible brain trauma may be established.

This concept works for all of the above-noted test stimuli, i.e., instead of gazing just to the left, or right, or up, or down, the proposed stimuli would have a subject gaze to the upper right, lower left, etc. Saccade testing could have saccades (or point-to-point eye movements) that are truly two-dimensional.

Ocular Physiology

The extraocular muscles are the three pairs of muscles that control the movements of the human eye. The actions of the extraocular muscles depend on the position of the eye at the time of muscle contraction.

| Muscle | Innervation | Origin | Insertion | Primary function | Secondary function | Tertiary function |
| --- | --- | --- | --- | --- | --- | --- |
| Superior rectus | Superior branch of oculomotor nerve | Annulus of Zinn from tendinous ring | eye (anterior, superior surface) | Elevation | Intorsion | Adduction |
| Inferior rectus | Inferior branch of oculomotor nerve | Annulus of Zinn from tendinous ring | eye (anterior, inferior surface) | Depression | Extorsion | Adduction |
| Lateral rectus | Abducens nerve | Annulus of Zinn from tendinous ring | eye (anterior, lateral surface) | Abduction | | |
| Medial rectus | Inferior branch of oculomotor nerve | Annulus of Zinn from tendinous ring | eye (anterior, medial surface) | Adduction | | |
| Superior oblique | Trochlear nerve | Superior and Medial to Annulus of Zinn via the Trochlea of superior oblique which forms a "pulley system" | eye (posterior, superior, lateral surface) | Intorsion | Depression | Abduction |
| Inferior oblique | Inferior branch of oculomotor nerve | Maxillary bone | eye (posterior, inferior, lateral surface) | Extorsion | Elevation | Abduction |

Eye Movements

| Medial (towards nose) | Lateral (towards temple) |
| --- | --- |
| Elevation, abduction: Inferior oblique | Elevation, adduction: Superior rectus |
| Adduction: Medial rectus | Abduction: Lateral rectus |
| Depression, abduction: Superior oblique | Depression, adduction: Inferior rectus |

The physiological reason for this is that it has been known for many decades that there are three pairs of neurological tracks that control the three pairs of muscles that innervate the eye; and these tracks are bilateral, i.e., represented in a coordinated manner for each eye. As a simple example, when the right eye moves right, the lateral muscle pulls the right eye toward the right, and the medial muscle of the right eye loosens its contraction of the eye to allow the eye to move right. At the same time, the opposite situation is occurring with the left eye, i.e., it is the medial muscle that contracts to move the left eye to the right and the lateral muscle of the left eye loosens its contraction of the eye to allow the eye to move right. This same scenario exists for vertical eye movements and for the most complicated eye movements, which are the oblique eye movements.

Cognition

There are many different ways of assessing cognition, i.e., present cognition vs. anticipatory cognition. Since, by its own nature, cognition is really not an involuntary, hard-wired, brain response, but integrates several neurological elements to achieve the response, this disclosure focuses on those cognitive functions that are closely related to the involuntary responses of the eye. One possible unique opportunity is to have the eye movement become the cognitive function, i.e., move the red dot into the yellow square by focusing on the dot and making the appropriate eye movement to move it toward and then into the yellow square. The time frame for completion of the task, the accuracy of the "line of sight" movement to the box, and the eventual end-point of dot placement within the box may be as significant, if not more so, than the current cognitive tests which are mainly based on hearing instructions, visual processing of the information, and a manual interaction with the computer, paper, etc., to give an answer. By just using the eyes and brain processing, the OculoKinetic Device provides a novel/better/quicker way to assess neurological changes in the test subject resulting from head injuries.

OculoKinetic Device Operational Architecture

FIG. 1 illustrates, in block diagram form, the overall architecture of the present OculoKinetic Device 100, which includes a Test Administrator Interface 101, a Test Subject Interface 102, and a Data Processor 103. The division of functionality illustrated herein is simply for the purpose of teaching the claimed invention and is not a limitation on the implementation of a system that embodies the novel functionality of the OculoKinetic Device. As an example, the Test Administrator Interface 101 includes a Data Input Interface 101B for use by the test administrator and a Display 101A for presenting test result information to the test administrator. The Test Subject Interface 102 includes an Enclosure 104 which encloses both a Stimulus Presentation Display 102A, which displays a set of visual stimuli for the test subject, and Ocular Measurement Devices 102B, which measure a set of test subject physiological parameters and the test subject's ocular responses to the visual stimuli. In addition, a Data Processor 103 is connected to both the Test Administrator Interface 101 and the Test Subject Interface 102. The Data Processor 102 includes a number of processes and databases (which can be implemented external to the Data Processor 103) for executing the tests and processing the resultant test subject measurement data. The Data Processor 103 includes Test Protocols 103A, Normative Databases 103B, Test Subject Stimulus Response Process 103C, Eye Characteristics Measurement 103D, Eye Movement Computation Process 103E, and Image Recording Device 103F as are described in additional detail below.

Enclosure

Figure 2A:
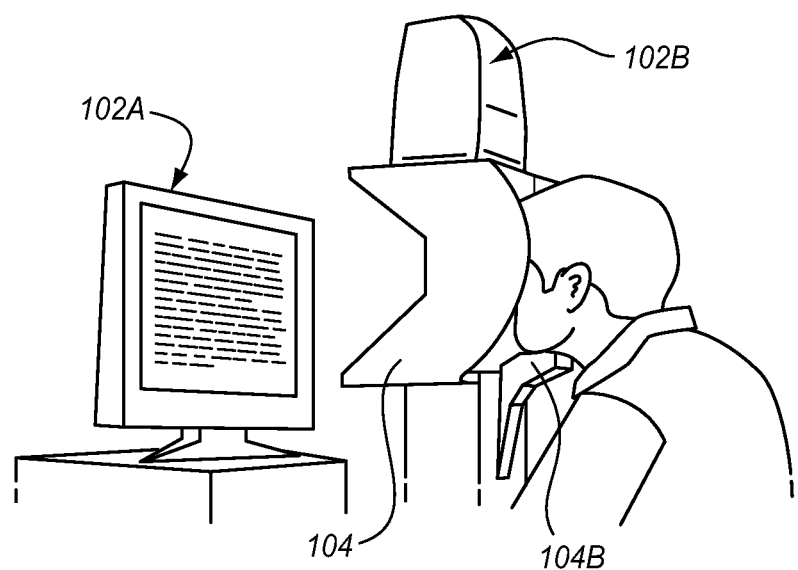
FIGS. 2A-2C illustrate a perspective view of two examples of the apparatus of the OculoKinetic Device, where
Figure 2B:
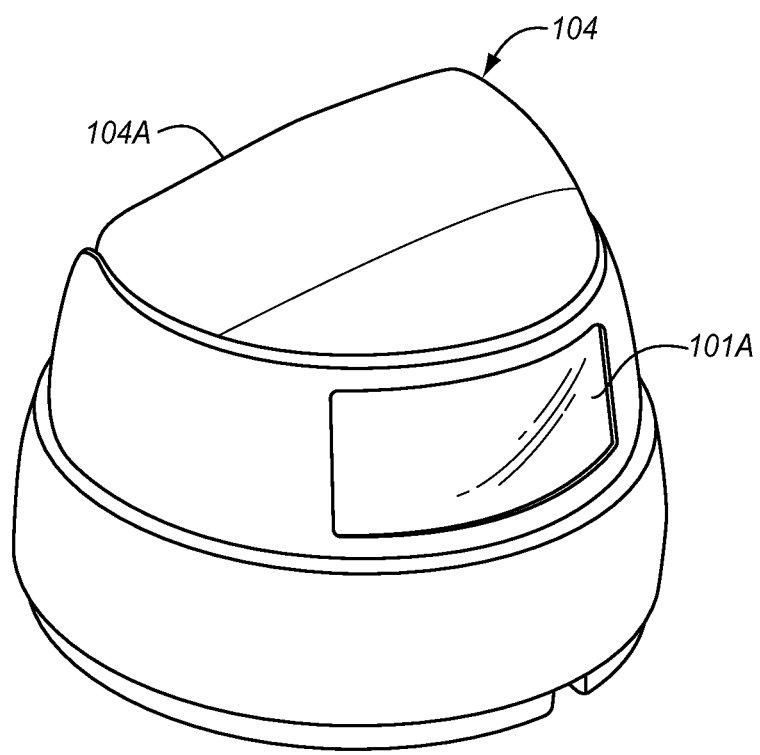
Figure 2C:
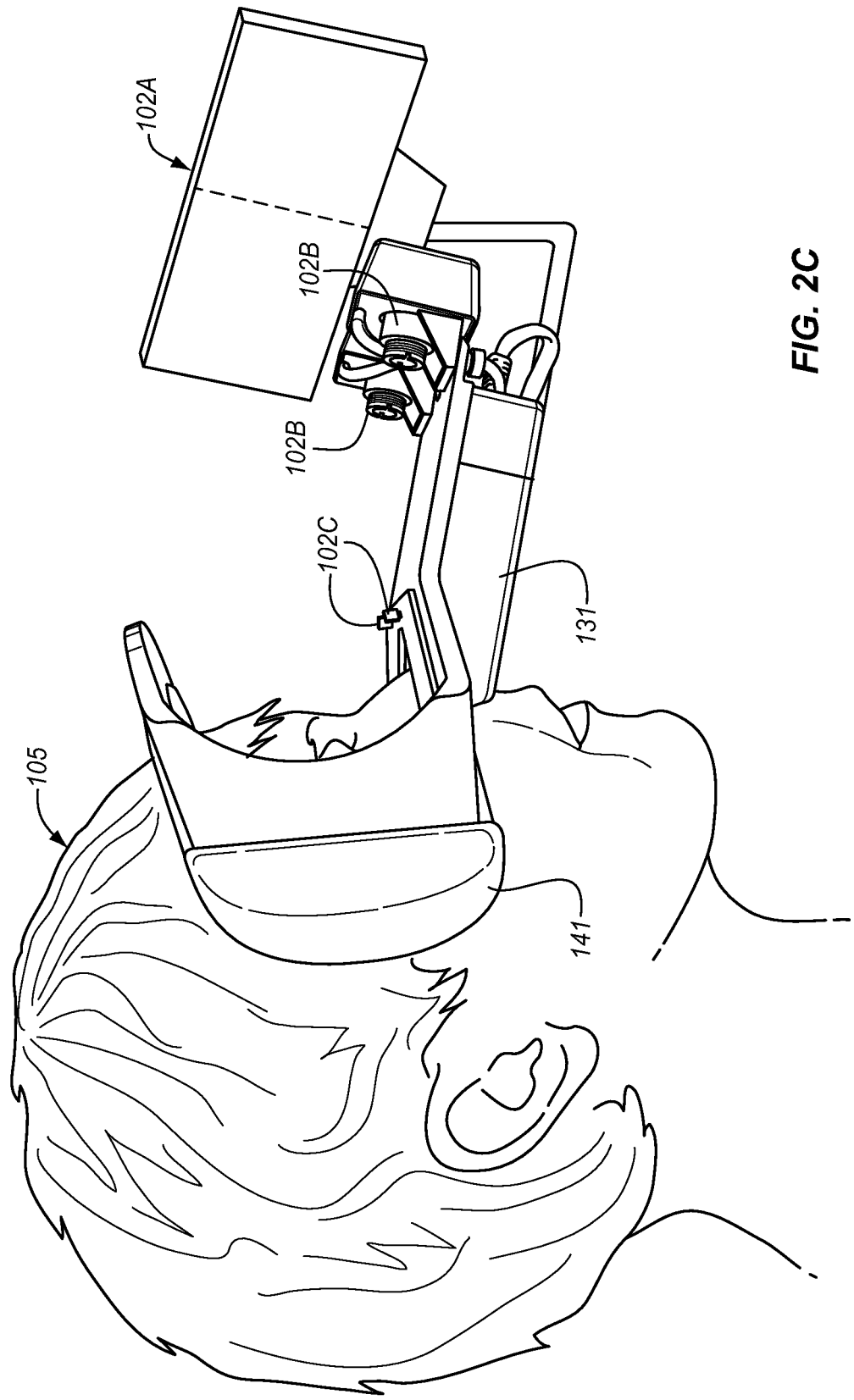

Rather than trying to control the ambient light of the room/test site or appearance of surrounding visible items that may confound the test subject's concentration on the visual targets presented on the Stimulus Presentation Display 1002A, an Enclosure 104 (such as the equipment shown in FIG. 2A, or the dome illustrated in FIG. 2B, or the headset shown in FIG. 2C) is configured to enclose the Stimulus Presentation Display 102A and Ocular Measurement Devices 102B, as well as to provide an aperture 104A that includes apparatus 104B to securely position the test subject's head and contact areas around the subject's facial area. FIGS. 2A and 2B illustrate a perspective view of two examples of the apparatus of the OculoKinetic Device 100, where FIG. 2A represents a fixed installation typically found in an office, and FIG. 2B represents a portable dome-shaped test subject interface, typically for field use where ambient lighting cannot be controlled. FIG. 2C illustrates a cross-section view of typical components used to implement a "headset" version of the OculoKinetic Device 100, which includes an enclosure (not shown) that encloses all of the apparatus shown in FIG. 2C. The occlusion of ambient light is an important factor in executing the tests, since a light-controlled environment is necessary to enable the precise measurement and tracking of the test subject's occular responses. The headset shown in FIG. 2C has a faceplate 141 against which the test subject 105 places their face and which may or may not include a chin rest to further support the head of the test subject. The Enclosure 104 increases the accuracy and reliability of these measurements and reduces any inaccuracy occasioned by the ambient conditions under which the test is administered. In particular, the illumination of the test subject's eyes is maintained at a consistent and predetermined level, the test subject's gaze is controlled, and the test administrator has the ability to concentrate on the administration of the test.

Stimulus Presentation and Ocular Response Measurement

The faceplate 141 illustrated in FIG. 2C positions the test subject's head with respect to Illumination Devices 102C and Ocular Measurement Devices 102B and also so the test subject 105 is looking at a Stimulus Presentation Display 102A. The faceplate 141 typically has two eye openings through which Illumination Devices 102C, attached to a frame 131, transmit beams of infrared light to illuminate the test subject's eyes. Two Ocular Measurement Devices 102B, also attached to frame 131, are mounted opposite the eye openings to generate images of the subject's illuminated eyes. The generated images are transmitted to an Image Recording Device 103F for storage and optionally to Display 101A for display to a test administrator. The test subject's eye responses, including eye movement and pupil responses, are recorded.

The Ocular Measurement Devices 102B are connected to an Image Recording Device 103F with the capability of storing video images or video stream in digital format such as on a disk drive, USB flash drive, solid state drive, compact flash cards, other local or networked storage devices, or other such apparatus for capturing and storing image data. The interconnection between the Ocular Measurement Devices 102B and the Image Recording Device 103F can be wired or wireless, using a cable or wireless communication protocol, respectively. Using the OculoKinetic Device 100, the test subject 105 looks into the system at the Stimulus Presentation Display 102A, which presents visual stimuli representative of previously defined tests, which may consist of (but are not limited to) any of the following test protocols or combination of these test protocols: (1) Smooth Pursuit, (2) Saccade, (3) Optokinetic, and (4) Pupillography. The test subject's eyes are tracked by the Ocular Measurement Devices 102B operating with Eye Movement Computation Process 103E sampling the generated images at a pre-selected sampling frequency, since the faster the sampling rate, the more accurate the data, and thus the resulting Waldorf Score (as described below). This sampling frequency is an important parameter, since aspects of the eye movements cannot be adequately assessed with slower scan frequencies. For instance, the acceleration of the eye when performing a Saccade test, or the evaluation of the micro-saccades when fixating on a target that is stationary, or the speed of a blink, hippus, or pupil oscillations, etc., occur at a rapid rate, which requires a higher sampling frequency for accurate detection and quantification.

Beam-splitter lenses also can be used, thereby allowing the Ocular Measurement Devices 102B to track the eyes while the test subject 105 is looking at the Stimulus Presentation Display 102A. Other embodiments could be one Ocular Measurement Device 102B looking at both eyes at the same time, one Ocular Measurement Device 102B which sequentially looks at one eye and then the other, or just one Ocular Measurement Device 102B tracking the eye movements of a single eye. Apropos to this Ocular Measurement Devices/eye group of configurations would be the eye/Stimulus Presentation Display 102A arrangement. This could range from a one eye-one Stimulus Presentation Display 102A configuration, to one that allowed both eyes at the same time to view a target on the Stimulus Presentation Display 102A, to a situation where one eye sees one Stimulus Presentation Display 102A or part thereof and the other eye sees another Stimulus Presentation Display 102A or part thereof. In this last configuration, it could be that the right eye would never see what is being presented to the left eye because of an internal divider that would preclude this cross eye/target ability.

Figure 8:
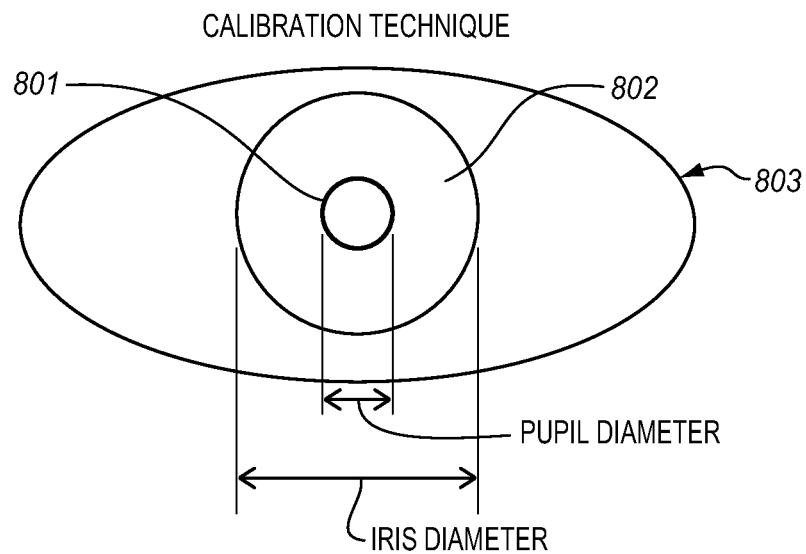
FIG. 8 is a drawing illustrative of typical pupil calibration measurements used in the OculoKinetic Device.

One of the preferred embodiments of the Stimulus Presentation Display 102A is to use existing flexible display technology to totally wrap the Stimulus Presentation Display 102A within the internal field of view of the enclosure 104 (wrap-around display). The benefits of this configuration include:

High Reliability—Environmentally friendly construction with long and safe operation in the most demanding of operational environments Optimal Visibility—Excellent display characteristics even when viewed from extreme angles and in less than optimum conditions Enhanced Viewability—Continuous improvement in design and manufacture in order to achieve display of true-to-life images Calibration, Sampling, and Analysis Knowing the actual size of the pupil 801, as shown in FIG. 8, is important from the standpoint of determining its centroid for position analysis, i.e., the size leads to a computation of the pupil's center giving an X, Y Coordinate. It is the change in this X, Y coordinate over time that results in the digital description of the movement of the eye, i.e., left-right, up-down. The measurement of an Iris-Pupil Ratio Algorithm for an enhanced pupil size determination is presently not used in evaluating the possibility of TBI. Since the size of the pupil can change based on many factors, i.e., ambient light, medications, injury, etc., knowing a stable parameter would greatly assist in any resulting pupil size metric. The iris 802 of the eye 803 is a stable parameter that does not change size. Thus, the diameter of the iris 802 can be used in a mathematical ratio with the pupil size to provide a more accurate assessment of the pupil's true size. For example, if the true size of the iris diameter is 20 mm, one could use that number each time an individual is tested to establish the change in the magnification factor for any subsequent test of that particular individual. If a subsequent test showed the iris diameter to be 15 mm, it would be known that the subject's head was slightly farther away from the camera than the baseline test. The computer analysis of the pupil size would be compensated by this difference. FIG. 8 illustrates a drawing illustrative of typical pupil calibration measurements used in the OculoKinetic Device 100. Pupil measurements are well known, and U.S. Pat. No. 7,614,745 teaches a system for such measurements.

Figure 9:
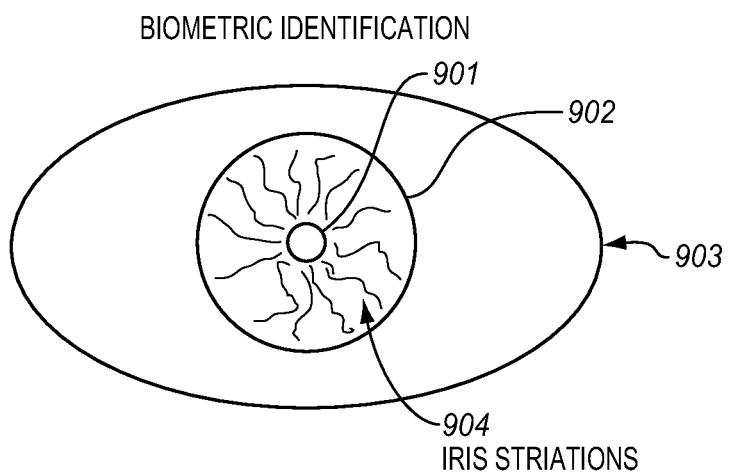
FIG. 9 is a drawing illustrative of typical pupil biometric identification measurements used in the OculoKinetic Device.

The OculoKinetic Device 100 may also use the eye as a biometric for the identification of the individual being tested, as shown in FIG. 9, since the striation pattern 904 in the iris 902 of the eye 903 is an immutable physical characteristic unique to each test subject. This may assist in the protection issues of human data as names, etc., would not be required. Identification using iris landmarks, or striations, is an existing technology, but not one that is seen in medical eye tracking devices.

Various Test Protocols

Figure 3:
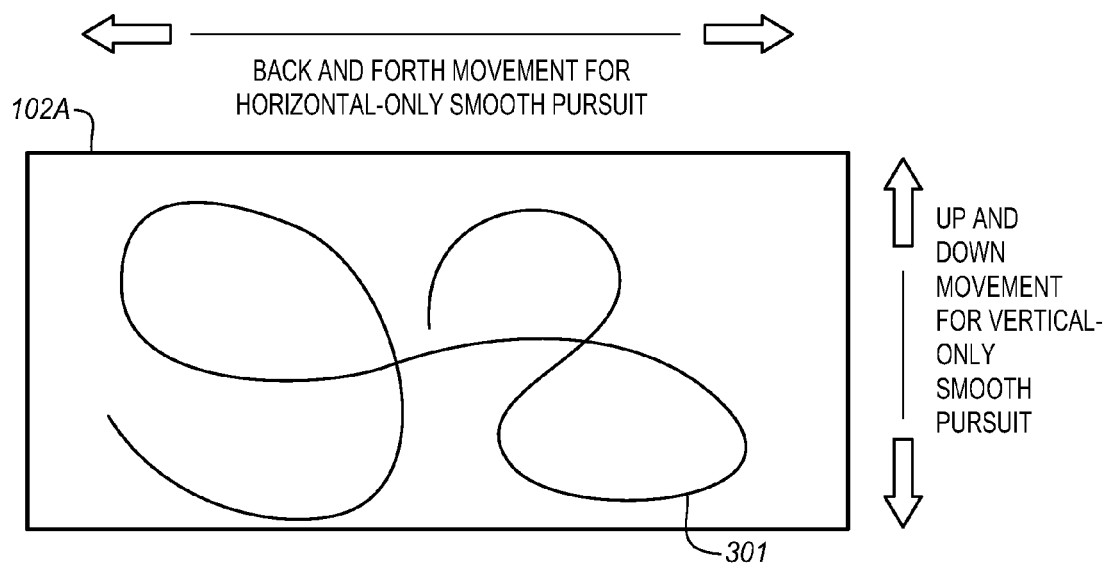
FIG. 3 is a drawing illustrative of a typical Smooth Pursuit image display used in the OculoKinetic Device.

There are several existing eye movement stimulus test protocols 103A or other types of tests that may be used for the application of defining brain functionality. They are:

1. Smooth Pursuit—a task in which the test subject is asked to keep their head still and track a moving object (sometimes referred to as "eye tracking"). FIG. 3 is a drawing illustrative of a typical Smooth Pursuit image 301 display used in the OculoKinetic Device 100. Existing Smooth Pursuit stimulations consist of only horizontal target movements or vertical target movements. There have been published smooth pursuit paradigms that are circular in nature, i.e., follow a moving target that circumscribes a circular path.

2. Free-Form type of paradigm—the analysis of the response is to see how well the test subject is able to track the moving target, i.e., accuracy of staying within certain defined standard deviations which may change depending on a test subject's age or other indications. The target may move at a stable speed, or may have accelerations/decelerations, color changes, target sizes, etc. The size of the area involved in the total smooth pursuit area of view may be changed as well.

Figure 4:
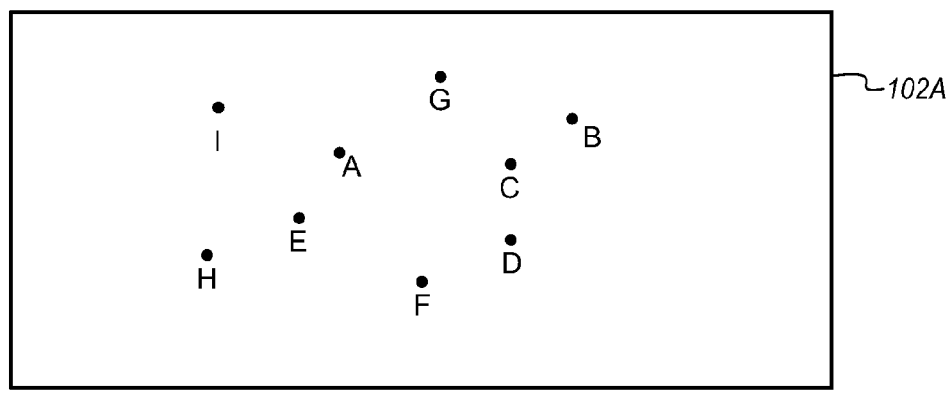
FIG. 4 is a drawing illustrative of a typical Saccade image display used in the OculoKinetic Device.

3. Saccade—A saccade is a fast movement of the eye. Saccades are quick, simultaneous movements of both eyes in the same direction. The saccade target is usually presented either horizontally or vertically. As with the OculoKinetic Device Smooth Pursuit paradigm, a more complex stimulus is being claimed, one that may look like the multi-point (A-I) stimulus illustrated in FIG. 4, or any other degree of complexity.

In this case, the test subject would start looking at the target in the "A" position. At some time, the "A" target disappears and the "B" target at that same time becomes visible. The analysis is done on the latency for the eye to begin its movement from "A" to "B"; how long it takes the eye to get to "B"; whether the acceleration and velocity profiles within the test subject's and/or population normative values; and does the eye stop at "B," or does it stop before "B" (called an "undershoot"), or does it pass "B" (called an "overshoot"). Both of these latter conditions then require the eye to do a corrective eye movement to get to the "B" target.

One of the reasons for the above-noted requirement of high speed is to have a sufficient number of sampling points of the movement of the eye to get an accurate assessment of the acceleration/deceleration profiles, as well as any corrective eye movement responses because of the undershoot/overshoot phenomenon.

The Saccade test can incorporate changes in target colors, shapes, etc., which would bring a unique "cognitive" function to the standard Saccade protocol. For instance, the test subject may be asked to look only at red target lights. "A" would be red, and let's say "B" is red as well, but "C" may be green. The test administrator would want to see if the test subject knows not to look at "C." If the test subject does start to make the eye movement to "C," how long does it take the test subject to stop their eye movement, etc.? This combination of standard eye movement tests coupled with cognitive tasks is a unique enhancement to the science of defining brain functionality.

Figure 5:
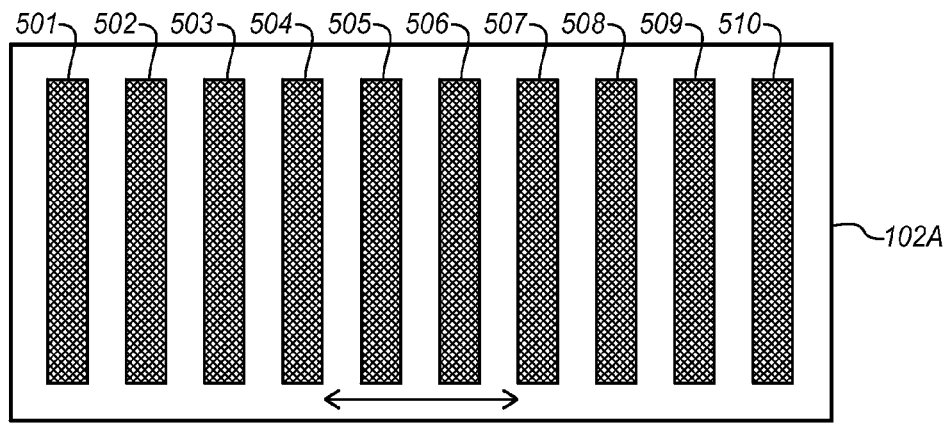
FIG. 5 is a drawing illustrative of a typical Optokinetic image display used in the OculoKinetic Device.

4. Optokinetic (OPK)—The optokinetic reflex allows the eye to follow objects in motion when the test subject's head remains stationary (e.g., observing individual telephone poles on the side of the road as one travels by them in a car). FIG. 5 is a drawing illustrative of the standard Optokinetic image display where, for horizontal OPK stimulation, the entire field of view is populated with stripes 501-510 aligned in a vertical direction and the stripes move in unison to the right or to the left. This same protocol is used for vertical OPK stimulation, where the stripes are aligned in a horizontal direction and they move in unison up or down. Although well defined in medical literature, this test typically is not performed or performed in a less than ideal manner, since the optimum target presentation requires a complete, full field of view and stimulus.

OculoKinetic Device Test Protocol

The ocular response characteristics are based on the target stimuli being presented, and all are based on current conventional methods for reporting such results. As an example, a Smooth Pursuit test plots like a moving sinusoidal wave pattern. The eye tracking results computed by the Eye Movement Computation Process 103E would be compared to the stimulus pattern (as stored in Test Protocols 103A) in terms of phase and gain. The phase and gain numbers then are compared by the Data Processor 103 to one or more selected data sets in the Normative Database 103B, such as population norm, the individual norm, a combination of both, etc. For Saccade results, the eye tracking wave form is compared to that of the visual stimulus contained in the selected test protocol. In this case, an important test result is latency, i.e., how long after the target light has gone from point "A" to point "B" does the eye make its move to point "B"? The Test Subject Stimulus Response Process 103C then looks at issues related to the acceleration and velocity of the eye movement. Finally, the accuracy of the test subject's eye directly stopping at point "B" is a significant metric. In many cases of brain injury, this can be a negative accuracy or undershoot where the eye stops before point "B" and then does a reflexive "catch-up" movement, or it can be a negative accuracy or overshoot where the eye goes past point "B" and then does a reflexive "back-up" movement to the target. For Optokinetic stimulations, the speed of the eye is measured in tracking the speed of the moving stripes, and then the automatic reverse Saccade when the eye can no longer physically move in the direction of the moving stripes. In this case, the eye should move with the stripes at the speed they are moving, with the corrective Saccade having its own characteristic of acceleration and velocity. Again, these results can be compared to a population norm and/or the test subject's normative baseline values.

What is unique about the Optokinetic test implemented in the present OculoKinetic Device is that it encompasses both Smooth Pursuit as well as discontinuous patterns, such as Saccade eye movements. For example, if the stripes are moving to the right, the eye follows a stripe until the eye can no longer physically move right (the Smooth Pursuit part of the Optokinetic stimulus). The eye then does a corrective Saccade to the left to find another stripe. It then follows that rightward moving stripe, and so on. The Test Subject Stimulus Response Process analysis compares the movement of the eye during the smooth pursuit stage to the speed of the movement of the stripes. It also determines the speed of the corrective Saccade (velocity and acceleration profiles). As with the other eye movement test described above, and related to the claim of intra-personal baseline comparisons, how well a test subject does this (these) task(s) may be compared to their ability to have accomplished the same prior to any head injury/concussion, etc. In addition, the OculoKinetic Device 100 uses a protocol that includes moving the stripes in an oblique direction from lower left to upper right, upper right to lower left, and any other paths that are angularly displaced from the horizontal and vertical axes.

Figure 6:
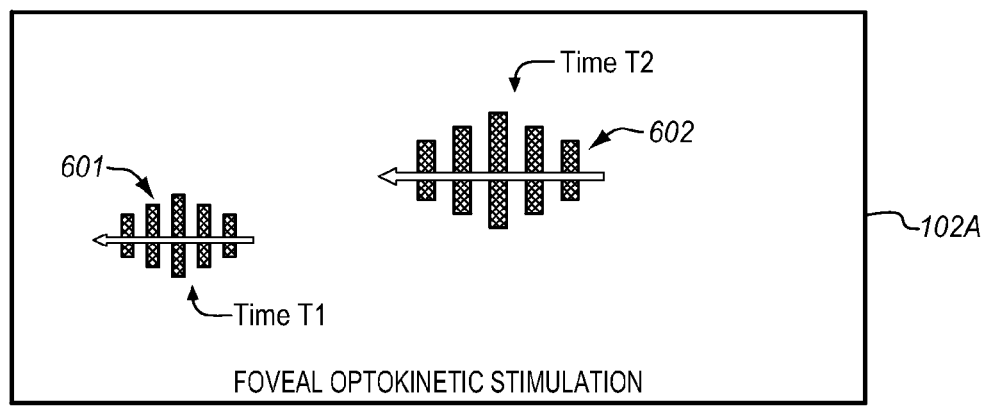
FIG. 6 is a drawing illustrative of a typical Foveal Optokinetic image display used in the OculoKinetic Device.

The OculoKinetic Device 100 may implement a new paradigm of VNG testing: Foveal and Peripheral OPK testing. Because the OculoKinetic Device 100 uses high speed video sampling rates for knowing the eye position, it can use the instantaneous eye position to control the placement of the stimuli. In the case of Optokinetic stimuli, these two additional types of stimulations are used in addition to the full field Optokinetic test:

Foveal OPK: The moving pattern of stripes is only present in an area of interest that follows the direct line of sight of the test subject. In FIG. 6, you see the moving stripe pattern 601 at Time T1 and the field of view of the moving OPK stripes. At Time T2, the eye has to move to a new location (602); and the area of interest of the OPK moving stripes moves as well. Thus, only the Foveal part of the retina is stimulated by this protocol.

Figure 7:
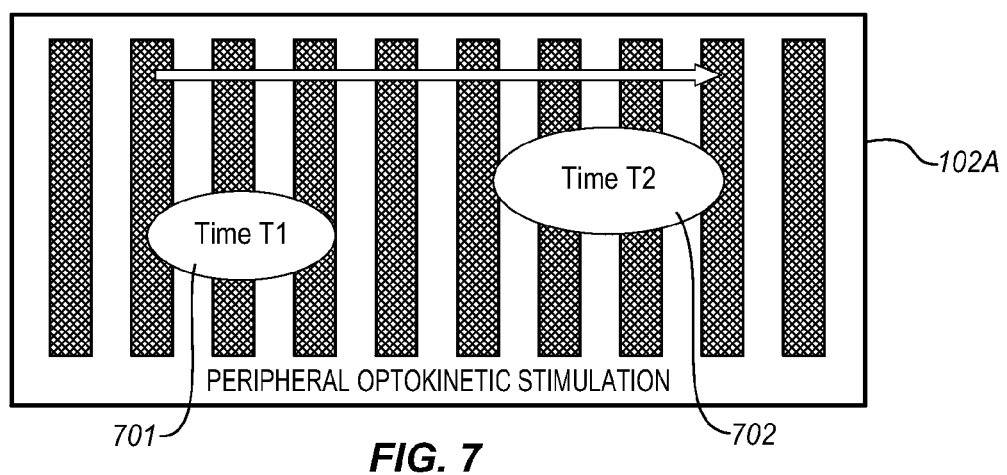
FIG. 7 is a drawing illustrative of a typical Peripheral Optokinetic image display used in the OculoKinetic Device.

Peripheral OPK: This is just the opposite of Foveal OPK. As shown in FIG. 7, Peripheral OPK stripes are only displayed outside the area of direct vision 701, 702.

Present stimuli used in optical testing are presented in a two-dimensional plane; however, one of the embodiments of the OculoKinetic Device 100 has the capability to expand that, when desired, to a three-dimensional presentation, i.e., imagine looking at a target dot that moves to the right, left, up, down, and/or in an oblique manner. Now add to that the fact that the target dot can be made, at times, to come closer to the subject, i.e., gets larger, or moves farther away by getting smaller (with the parallax that is required for three-dimensional viewing—one eye sees the target in a slightly different position than the other eye, and the brain arranges these two slightly different images to mean depth. Using existing technology, this function is present in the OculoKinetic Device 100.

Color-Based Optokinetic Stimulus

A color-based cognitive feature is contemplated for use with the Optokinetic stimulus, where the test subject is told to only look at a red stripe which may be amongst different colored stripes. This and the other stimulations, including background colors, target colors, shapes, etc., can be changed—and these changes may allow for a more age-defined test, i.e., children may find it easier to track a "Smiley Face" rather than just a target dot.

The underlying reason for having these types of Optokinetic stimulations is the fact that it is different neural pathways within the brainstem that control this ocular reflex. The goal is to test as many of the neural pathways in an age-independent manner that might be affected by head trauma/concussion, since it remains an unknown at this time which of the target stimulations or combination thereof yields the most accurate results for the intended application.

Additional Physiological Measurements

Pupillography includes the recording of pupillary responses of the eye. The novelty of this testing is combining it with the eye movement tests which adds to the validity of the resulting "Waldorf Scale" of brain status. Although inherent in most video-based eye tracking is the ability to know the pupil information, the novel use of combining with the eye tracking results is novel.

Measurements may include, but are not be limited to:
Pupil Size
Pupil reaction to light stimulation; such as time to react, time to maximum constriction, rebound dilation, average size during illumination, etc.
Hippus (oscillations of the pupil that are inherent in its normal functionality)
Cognition—The mental process of knowing, including aspects such as awareness, perception, reasoning, and judgment. As mentioned in several of the eye stimulation paradigms above, the combination of having the test subject perform (or not perform) a task while the eye is being stimulated is claimed to be an important construct of the OculoKinetic Device, especially as combined with eye tracking tasks.
Blinks—the high speed requirement for scanning allows for the discrete analysis of the blink frequency as well as issues related to the speed of the blink, the time of eye closure, etc.
Ptosis—This is a 'droopy' eye lid. It is anticipated that some injuries may result in an eye lid that does not open as much as in the pre-injury condition. This is determined from the eye tracking algorithms that compute the size of the pupil (see discussion below). A droopy eye lid, as captured digitally from the OculoKinetic Device, may be part of the "Waldorf Score" computation.

Waldorf Score

Finally, the eye movement protocol results, optionally coupled with results from other non-eye movement tests, i.e., neurocognitive and balance testing, information from a physical exam, etc., can be used to generate a metric termed herein the "Waldorf Score," which scales the brain injury of the subject by incorporating a plurality of measured metrics. It is computed from the results of the various oculomotor tests at a minimum, ranging to a compilation of data including, but not limited to, pupillography, balance, and cognitive test results, plus metrics such as blood pressure, body temperature, etc., which can be taken from the eyeball. On-going research and/or data mining provide the various analytical "weights" or importance of any individual parameter used in the "Waldorf Score."

Furthermore, it is contemplated that the "Waldorf Score" itself may have various levels of sensitivity depending on the application, i.e., a "Basic Waldorf Score," which is based solely on the results from the oculomotor tests and pupillography; an "Enhanced Waldorf Score," based on the parameters of the Basic Waldorf Score plus the results of balance testing protocols; and the "Ultra Waldorf Score," which includes the Enhanced Waldorf Score data plus the results of neurocognitive test protocols and physical and physiological examinations.

Knowing the "Waldorf Score" for a patient at any point in time provides clinicians and caregivers the ability to more easily understand the neurophysiological issues at play and guide therapeutic and rehabilitation programs, as well as assist in making "return to play" or "return to duty" determinations.

To monitor the movements of the patient's eyes, ocular measurement devices that are sensitive in the near infrared illumination spectrum are positioned in the field of vision of the test subject to record their eye movements during testing. These ocular measurement devices are housed in a test subject interface which can be in the form of goggles, or head-mounted configurations, or positioned in a "dedicated tunnel" or "cone of darkness" viewport-type device. In addition, a stimulus presentation device is included in the test subject interface to display visual stimuli for the test subject. To maximize the efficacy of these measurements, it is imperative that the configuration of the ocular measurement devices, the stimulus presentation device, and the test subject be arranged in a manner that controls the ambient light impinging on the test subject's eyes, as well as the elimination of extraneous visual targets from the test subject's field of vision. All of this must be accomplished in an ergonomically sound and reproducible manner such that the test subject can easily be tested in a quick and efficient manner on, in, or adjacent to a field of play, combat zone, or industrial environment.

The ideal system for the physiologic evaluation of brain function has the following features: self-diagnostics to ensure each test is being performed with the electronics and software working at their optimum; ability to document the test subject, stimulus paradigms, and test results in a manner that meets the requirements for human subject medical applications; and it must meet the criterion for functional testing in ambient environments that are variable in terms of weather, temperature, and other testing environment constraints. A numerical output is essential for accurate comparison to normal subjects, the patient's own normative baseline score, and progression or deterioration of their condition over time.

The "Waldorf Score" is a numerical output, for example on a scale of 0-10, which provides an indication of the level of brain functionality based on the results of the tests performed by the OculoKinetic Device. This score optionally includes data other than data generated by the test controller 102 of the OculoKinetic Device 100, i.e., results from balance and neurocognitive tests, medical history, physical examination, vital signs, etc. Also, issues related to the mTBI injury (sports activity, running into a stationary object, being hit by a moving object, acceleration and direction of the head insult, etc.) can be input as factors that can be used in determining a score for the potential mTBI. The "Waldorf Score," when used for issues related to head trauma/concussion from sports injuries, is part of the immediate decision made at the point/time of injury, as well as in the post-injury/concussion treatment process and rehabilitation related to what is referred to as the decision for Return to Play. Thus, the "Waldorf Score" for any person may go from 100, meaning totally normal brain function, to a 65 at the time of injury, and then up to a 75 two weeks later after medical intervention, rest, etc., and progressing to an 85, which may be the level that allows for the decision for a patient to Return to Play. These are hypothetical values but represent the concept underlying the use of the "Waldorf Score."

Operation Of The OculoKinetic Device

Figure 10A:
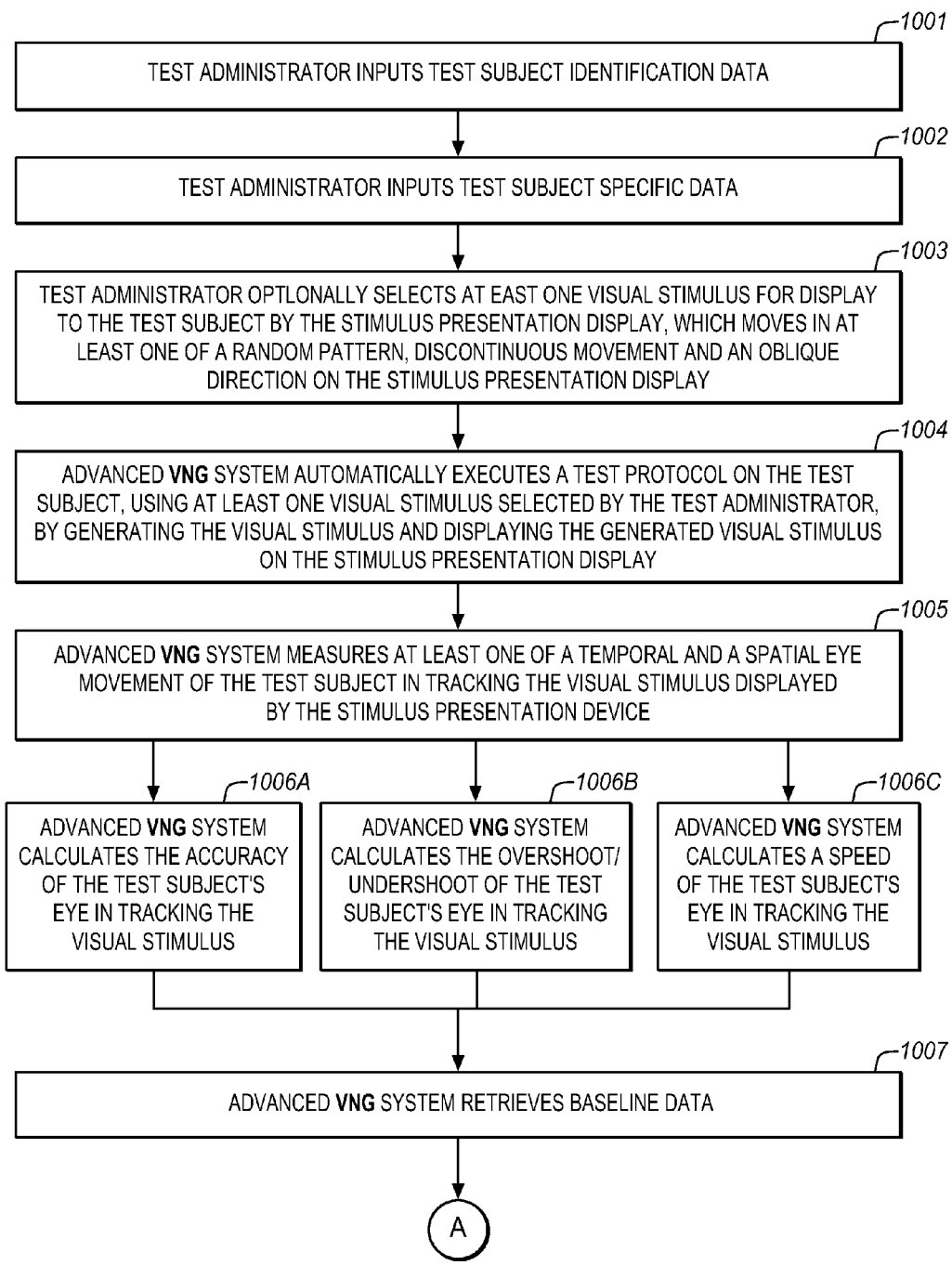
FIG. 10 illustrates, in flow diagram form, the operation of the OculoKinetic Device.
Figure 10B:
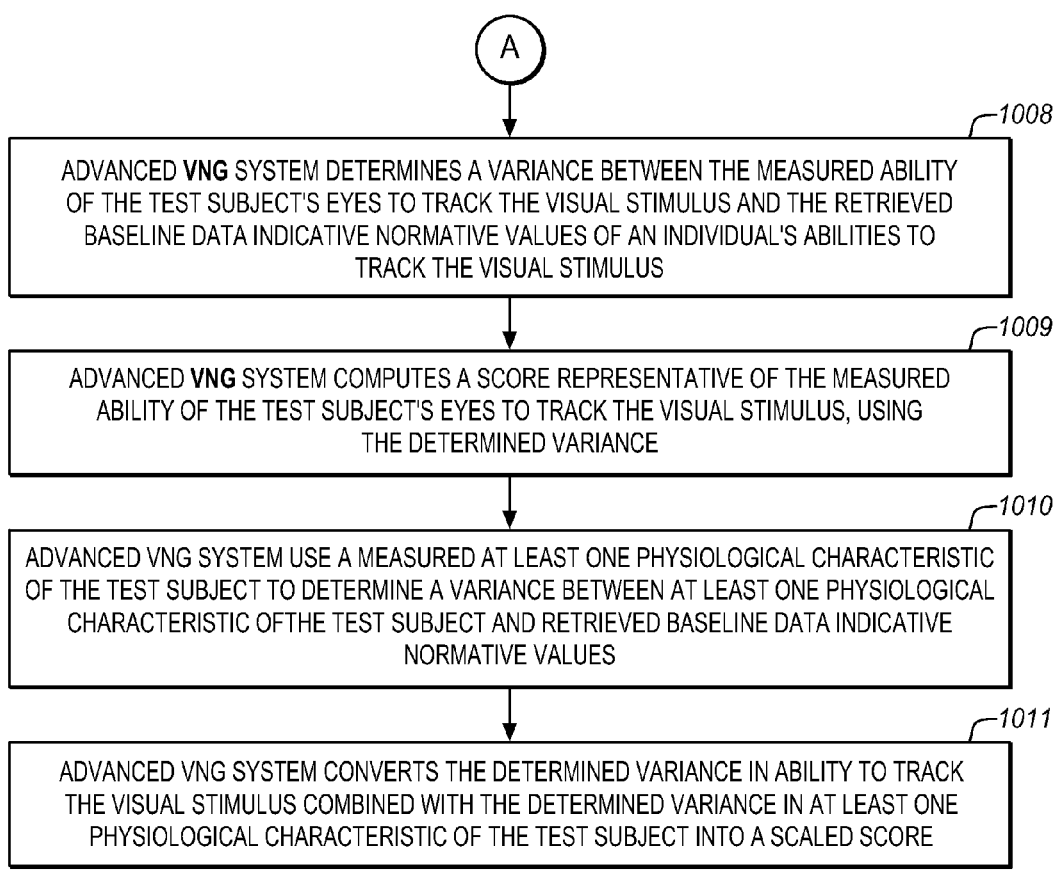

FIG. 10 illustrates, in flow diagram form, the operation of the OculoKinetic Device in executing an exemplary test or series of tests on a test subject. At step 1001, the test administrator activates the OculoKinetic Device 100 and inputs test subject identification data into the Data Input Interface 101B to uniquely identify this test subject and thereby create a file in the Data Processor 103 associated with this test subject. At step 1002, the test administrator inputs, via the Data Input Interface 101B, test subject specific data, such as: age, sex, nature of injury, and optionally at least one physiological characteristic of the test subject selected from the set of physiological characteristics including: pupillography, cognition, balance test results, cognitive test results, blood pressure, and body temperature. At step 1003, the test administrator optionally selects at least one visual stimulus for display to the test subject by the stimulus presentation display which moves in at least one of: a random pattern, discontinuous movement, and an oblique direction on the stimulus presentation display. At step 1004, the OculoKinetic Device 100 automatically executes a test protocol on the test subject, using the at least one visual stimulus selected by the test administrator, by generating the visual stimulus and displaying the generated visual stimulus on the Stimulus Presentation Display 102A. The OculoKinetic Device 100 may include automated verbal instructions to the subject instead of a test administrator giving instructions. At step 1005, the OculoKinetic Device 100 measures, using the ocular measurement device, at least one of a temporal and one of a spatial eye movement of the test subject in tracking the visual stimulus displayed by the stimulus presentation device. At steps 1006A-1006C, the OculoKinetic Device 100 automatically performs at least one analysis determination and calculates a speed of the test subject's eye in tracking movement of the visual stimulus, and/or calculates the accuracy of the test subject's eye in tracking movement of the visual stimulus, and/or calculates the overshoot/undershoot of the test subject's eye in tracking movement of the visual stimulus, respectively. At step 1007, the OculoKinetic Device 100 retrieves baseline data indicative of an individual's abilities to track the visual stimulus from a normative database and, at step 1008, determines a variance between the measured ability of the test subject's eyes to track the visual stimulus and the retrieved baseline data indicative normative values of an individual's abilities to track the visual stimulus. At step 1009, the OculoKinetic Device 100 computes a score representative of the measured ability of the test subject's eyes to track the visual stimulus, using the determined variance for display to the test administrator.

In addition, the OculoKinetic Device 100 at step 1010 can optionally use a measure of at least one or more physiological characteristics of the test subject selected from a set of physiological measures including, but not limited to: pupillography, cognition, balance test results, cognitive test results, blood pressure, and/or body temperature to determine variances between the chosen physiological characteristic(s) of the test subject and the retrieved baseline data from that same individual and/or a population norm for that same data set of measures. At step 1011, the OculoKinetic Device 100 converts the determined variance in ability to track the visual stimulus combined with the determined variance in at least one physiological characteristic of the test subject into a scaled score for display to the test administrator.

Baseline and Data Mining

Some of the data already in the public domain shows eye movement results in relationship to normative data, i.e., people of the same age with no head trauma tested with the same equipment in the same protocol, or against existing norms from other published studies that may or may not have used the same equipment. Testing an individual against their own normative responses may prove to be a more accurate approach. One could contemplate that an individual may go through several rounds of testing on an OculoKinetic Device, i.e., before the season starts for a sport, at random times during the season, possibly before and after each game or match (boxing comes to mind). The baseline data, therefore, would continue to grow for that individual. This is useful for data mining, since it is conceivable that an OculoKinetic Device could be used in a high school football setting, for example; and as the individual progresses to college and professional sports, the data mining that may be included in the system software would create a valuable historical view of not only the individual's brain function but would add depth to any population norm that may evolve from this unique process. One method of transmission of this data would be to have subject de-identified data uploaded continuously to an Internet-based managed database, i.e., the "Cloud," and stored for later analysis.

SUMMARY

The present OculoKinetic Device produces an eye movement stimulus protocol that moves in any direction of the two-dimensional plane, including a more complex randomized pattern. The OculoKinetic Device test protocols also are not limited to just black and white images. It appears that brain injury is more accurately detected by using colored dots, stripes, etc. In addition, the use of symbols is anticipated, where the ocular stimuli are geometric shapes, multi-colored images, flashing images, etc.

What is claimed:

1. A method for computing a measure of the ocular response of a test subject using an ocular measurement device which is positioned in front of the eyes of the test subject, in response to predetermined visual stimuli which are presented on a stimulus presentation display that is positioned in front of the eyes of the test subject, for viewing by a test subject, comprising:

generating a visual stimulus for display to the test subject by the stimulus presentation display that moves in at least one of: a random pattern, discontinuous movement, and an oblique direction on the stimulus presentation display;

measuring, using the ocular measurement device, at least one of a temporal and one of a spatial eye movement of the test subject in tracking the visual stimulus displayed by the stimulus presentation device; and computing a score representative of the measured ability of the test subject's eyes to track the visual stimulus, comprising:

retrieving baseline data, indicative of an individual's abilities to track the visual stimulus, from a normative database; and determining a variance between the measured ability of the test subject's eyes to track the visual stimulus and the retrieved baseline data indicative of normative values of an individual's abilities to track the visual stimulus.

2. The method of computing a measure of the ocular response of a test subject of claim 1 wherein the step of measuring comprises:

calculating a speed of the test subject's eye in tracking movement of the visual stimulus.

3. The method of computing a measure of the ocular response of a test subject of claim 1 wherein the step of measuring comprises:

calculating the accuracy of the test subject's eye in tracking movement of the visual stimulus.

4. The method of computing a measure of the ocular response of a test subject of claim 1 wherein the step of measuring comprises:

calculating the overshoot/undershoot of the test subject's eye in tracking movement of the visual stimulus.

5. The method of computing a measure of the ocular response of a test subject of claim 1 wherein the visual stimuli are at least one of: geometric shapes, multi-color images, or flashing images.

6. The method of computing a measure of the ocular response of a test subject of claim 1 wherein the step of computing further comprises:

converting the determined variance in ability to track the visual stimulus into a scaled score.

7. The method of computing a measure of the ocular response of a test subject of claim 1 wherein the step of computing further comprises:

measuring at least one physiological characteristic of the test subject selected from the set of physiological characteristics including: pupillography, cognition, balance test results, cognitive test results, blood pressure, and body temperature; and determining a variance between at least one physiological characteristic of the test subject and retrieved baseline data indicative of normative values of an individual's at least one physiological characteristic of the test subject.

8. The method of computing a measure of the ocular response of a test subject of claim 7 wherein the step of computing further comprises:

converting the determined variance in ability to track the visual stimulus combined with the determined variance in at least one physiological characteristic of the test subject into a scaled score.

9. The method of computing a measure of the ocular response of a test subject of claim 7 wherein the at least one physiological characteristic of the test subject comprises pupil size, pupil reaction to light stimulation, and hippus.

10. The method of computing a measure of the ocular response of a test subject of claim 7 wherein the at least one physiological characteristic of the test subject comprises blinks or ptosis.

* * * * *